(12) United States Patent
Tsuta

(10) Patent No.: US 8,083,352 B2
(45) Date of Patent: *Dec. 27, 2011

(54) PERIMETER

(75) Inventor: Tomohiro Tsuta, Kobe (JP)

(73) Assignee: Tomohiro TSUTA (Master's Degree of Economics of the University of Tokyo), Kobe (JP)

( * ) Notice: Subject to any disclaimer, the term of this patent is extended or adjusted under 35 U.S.C. 154(b) by 124 days.

This patent is subject to a terminal disclaimer.

(21) Appl. No.: 12/733,269

(22) PCT Filed: Jun. 1, 2009

(86) PCT No.: PCT/JP2009/059984
§ 371 (c)(1),
(2), (4) Date: Feb. 22, 2010

(87) PCT Pub. No.: WO2010/024010
PCT Pub. Date: Mar. 4, 2010

(65) Prior Publication Data
US 2011/0273670 A1    Nov. 10, 2011

(30) Foreign Application Priority Data

Aug. 25, 2008 (JP) ................................. 2008-215041

(51) Int. Cl.
*A61B 3/02* (2006.01)
*A61B 3/00* (2006.01)

(52) U.S. Cl. .......................... 351/224; 351/200; 351/222
(58) Field of Classification Search .......... 351/224–226, 351/222, 200, 246
See application file for complete search history.

(56) References Cited

U.S. PATENT DOCUMENTS

2004/0046934 A1* 3/2004 Sponsel et al. ................ 351/200
2004/0057013 A1* 3/2004 Cappo et al. .................. 351/224

FOREIGN PATENT DOCUMENTS

| JP | S58/121937 | 7/1983 |
|---|---|---|
| JP | H4/135534 | 5/1992 |
| JP | H14/306413 | 10/2002 |
| JP | H16/73545 | 3/2004 |
| JP | H19/29112 | 2/2007 |
| JP | H19/75350 | 3/2007 |
| JP | H20/36297 | 2/2008 |
| WO | WO2006/106877 | 10/2006 |

* cited by examiner

*Primary Examiner* — Dawayne A Pinkney

(57) ABSTRACT

A perimeter of the present invention including: visual field scanning screen generating means; fixation image displaying and controlling means; visual target scan line parallel setting means; statically displaying and controlling means; static display position storing means; static display and control stopping means; kinetic display and control starting means; detecting means; detection position storing means; distance storing means; kinetic scan stopping means; and scanning continuation means to the position of the visual target stored by the detection position storing means.

2 Claims, 6 Drawing Sheets

PERIMETER

BACKGROUND OF THE INVENTION

The present invention relates to a perimeter, an operational method of a perimeter, a program for realizing a perimeter, and a computer-readable recorded medium.

The following are known as previous perimeters: Goldmann perimeter of 510 model [1945], 940 model [1967]; Tubinger perimeter [1957]; Octopus perimeter [1976]. (see, for example, the nonpatent literature 1.)

The explanation of previous perimeters: Goldmann perimeter is the first brightness perimeter, adopting manual method of simultaneous recording, with 4 to 60 degrees of brightness of the visual target and 6 types of visual angle of the visual target, capable of examining visual field of visual angle, and with adjustability of its background brightness. The shortcoming is that it fails to examine the central region within 5 degrees;

Tubinger perimeter [1957] is the first practical, static perimeter, capable of examining the kinetic visual field and the visual field of color, flicker, and etc., adopting manual method of simultaneous recording, with 80 degrees of brightness of the visual target and 100 degrees of brightness of the fixation image and 5 kinds of color and 6 degrees of background brightness, and capable of examining the central and eccentric vision. Its shortcoming is in the difficulty of controlling the visual target movement, and of adjusting the visual target, fixation image, and background illumination lamp;

Octopus perimeter [1976] is the world's first fully automated, static perimeter.

Nonpatent literature 1: "The latest comprehensive dictionary of medical science", Ishiyaku Publishers Inc., 1987, 1990.

There exists a considerable discrepancy between the chart resulted from a previous visual field examination and the shape of scotoma and blind spot true to the subject, since the shapes of scotoma and blind spot detected by previous perimeters are very rough.

It is because of relying on previous perimeters that the early detection of visual defects has been failing.

And there is the high possibility of erroneous responses made by the subject due to habituation, etc., because procedures of previous examinations are made up of very monotonous repetitions.

The aim of the present invention is, therefore, to provide a perimeter capable of reflecting, in much greater detail, the shape of the scotoma and blind spot true to a subject into the image obtained by the examination.

The aim of the present invention is also to provide a perimeter reducing the monotony seen in previous examinations of the visual field.

SUMMARY OF THE INVENTION

The aim of the present invention is to provide the perimeter capable of reflecting, in much greater detail, the shape of the scotoma and blind spot true to a subject into the image obtained by the examination.

The aim of the present invention is also to provide the perimeter reducing the monotony seen in previous examinations of the visual field.

To achieve the above aim,

The invention of claim 1 is a perimeter including:

Means for generating, on an output device, a visual field scanning screen for scanning a visual field of a subject;

Means for displaying and controlling a fixation image to be fixated by said subject, during a visual field scanning, on the visual field scanning screen generated by said visual field scanning screen generating means;

Means for setting a visual target scan line to scan a visual target, parallel on said visual field scanning screen;

Means for statically displaying and controlling said visual target on the visual target scan line set by said visual target scan line parallel setting means;

Means for storing, on a memory device, a position of said visual target statically displayed and controlled by said statically displaying and controlling means;

Means for stopping said static display and control of said visual target if said visual target has statically displayed and controlled for a predetermined moment by said statically displaying and controlling means;

Means for starting a kinetic scan of said visual target, along said visual target scan line, from the position stored, by said static display position storing means, in the memory device, if said static display and control of said visual target is stopped by said static display and control stopping means;

Means for, via an input device, detecting a time when said kinetic scan, started by said kinetic display and control starting means, of said visual target has first been perceived by the subject's visual field;

Means for storing, on the memory device, a position of said visual target at the time of the detection by said detecting means;

Means for storing, on the memory device, a distance from the position of said visual target displayed and controlled by said statically displaying and controlling means, to the position of said visual target at the time of the detection by said detecting means, as a piece of information which reflects a function of the visual field extending from the position of said visual target displayed and controlled by said statically displaying and controlling means, to the position of said visual target at the time of the detection by said detecting means;

Means for stopping said kinetic scan of said visual target if the time when said kinetic scan has first been perceived by the subject's visual field is detected via the input device by said detecting means;

And scanning continuation means for, through said statically displaying and controlling means, displaying and controlling said visual target statically on said visual target scan line at the position of said visual target stored by said detection position storing means, And proceeding from said static display position storing means onward as above, And continuing the similar scan of said visual target scan line by iterating above procedure along said visual target scan line, in order to continue the next scan of said visual target scan line if the time when said kinetic scan has first been perceived by the subject's visual field is detected via the input device by said detecting means.

The invention of claim 2 is a program for causing a computer to realize the function including:

Means for generating, on an output device, a visual field scanning screen for scanning a visual field of a subject;

Means for displaying and controlling a fixation image to be fixated by said subject, during a visual field scanning, on the visual field scanning screen generated by said visual field scanning screen generating means;

Means for setting a visual target scan line to scan a visual target, parallel on said visual field scanning screen;

Means for statically displaying and controlling said visual target on the visual target scan line set by said visual target scan line parallel setting means;

Means for storing, on a memory device, a position of said visual target statically displayed and controlled by said statically displaying and controlling means;

Means for stopping said static display and control of said visual target if said visual target has statically displayed and controlled for a predetermined moment by said statically displaying and controlling means;

Means for starting a kinetic scan of said visual target, along said visual target scan line, from the position stored, by said static display position storing means, in the memory device, if said static display and control of said visual target is stopped by said static display and control stopping means;

Means for, via an input device, detecting a time when said kinetic scan, started by said kinetic display and control starting means, of said visual target has first been perceived by the subject's visual field;

Means for storing, on the memory device, a position of said visual target at the time of the detection by said detecting means;

Means for storing, on the memory device, a distance from the position of said visual target displayed and controlled by said statically displaying and controlling means, to the position of said visual target at the time of the detection by said detecting means, as a piece of information which reflects a function of the visual field extending from the position of said visual target displayed and controlled by said statically displaying and controlling means, to the position of said visual target at the time of the detection by said detecting means;

Means for stopping said kinetic scan of said visual target if the time when said kinetic scan has first been perceived by the subject's visual field is detected via the input device by said detecting means;

And scanning continuation means for, through said statically displaying and controlling means, displaying and controlling said visual target statically on said visual target scan line at the position of said visual target stored by said detection position storing means, And proceeding from said static display position storing means onward as above, And continuing the similar scan of said visual target scan line by iterating above procedure along said visual target scan line, in order to continue the next scan of said visual target scan line if the time when said kinetic scan has first been perceived by the subject's visual field is detected via the input device by said detecting means.

According to the first invention of a perimeter, a visual field mapping image, for example, as shown in FIG. 2 can be obtained based on the data generated from a scanning of a visual field by the perimeter of the present invention.

The perimeter of the present invention can generate data relating not only to the scotoma and blind spot but also to regions where visual function of the visual field slightly declines.

The perimeter of the present invention can generate data regarding visual function of the visual field.

The perimeter of the present invention can also generate data regarding the condition of visual function in the vicinity of fovea of the visual field.

According to the second invention of a program, a visual field mapping image, for example, shown in FIG. 2 can be obtained based on the data generated from a scanning of a visual field by the perimeter of the present invention.

The perimeter of the present invention can generate data relating not only to the scotoma and blind spot but also to regions where visual function of the visual field slightly declines.

The perimeter of the present invention can generate a data regarding the visual function of the visual field.

The perimeter of the present invention can also generate data regarding the condition of visual function in the vicinity of fovea of the visual field.

In FIG. 2, a visual field mapping rectangle is filled with a green whose brightness is increased according to severity of the decline in visual function of the corresponding visual field, by a CPU 501.

In FIG. 2, a scotoma 201, a blind spot 203, a connection of scotoma with blind spot 202, etc. are explicitly shown by a cluster of visual field mapping rectangles of bright greens.

The perimeter of the present invention can map visual function of the visual field.

The perimeter of the present invention can map not only the scotoma 201 and blind spot 203, but also portions of visual field where visual function declines 204 and portions of visual field where visual function slightly declines 205.

In FIG. 2, not only the scotoma 201 and blind spot 203 but also visual function of the visual field is mapped.

In a visual field mapping image generated by the perimeter of the present invention, portions of visual field where visual function declines 204 and portions of visual field where visual function slightly declines 205 can also be analyzed regarding their locations, sizes, shapes, etc., from a cluster of the visual field mapping rectangles filled with greens of moderate brightness.

The perimeter of the present invention can also map the condition of visual function in the vicinity of a fovea 206 of the visual field.

The fovea 206 having the highest functioning among visual field is represented, in FIG. 2, by a cluster of the visual field mapping rectangles filled with greens of lower brightness.

For the perimeter of the present invention, the CPU 501 forms a visual field mapping rectangle from data obtained by its scanning of a visual field and carries out an image processing for the visual field mapping rectangle based on the data, through which, in the meanwhile, the CPU 501 can generate a visual field mapping image proper for being called scan of visual field, strongly indicating the retinal structure and so forth.

The perimeter of the present invention may be embodied by a simple setup without the need for voluminous equipment such as Goldmann perimeter and the like.

The perimeter of the present invention can examine the central portion within 5 degrees of a visual field.

DETAILED DESCRIPTION OF THE INVENTION

Figure 1:
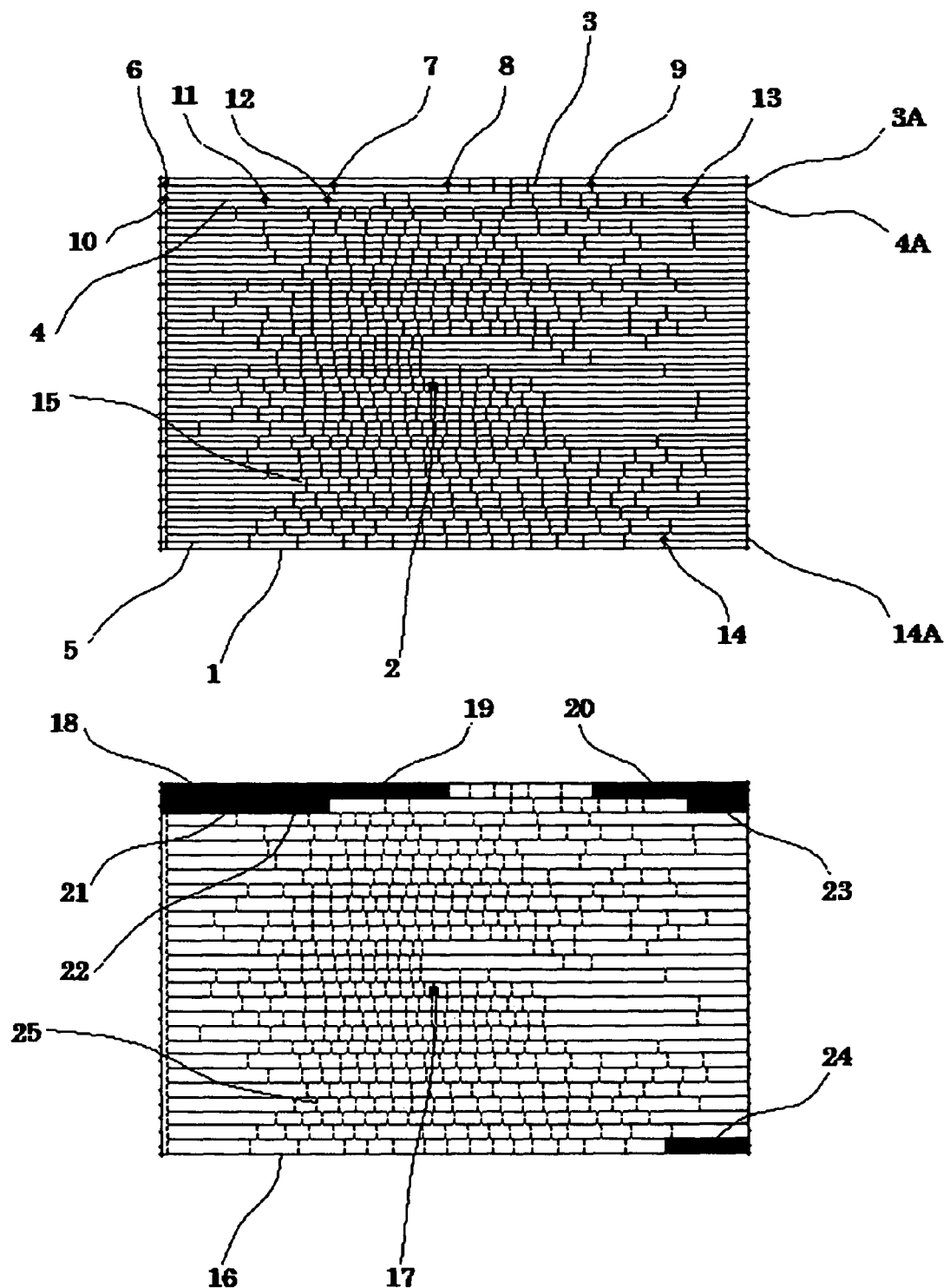
FIG. 1 is a schematic diagram showing a preferred embodiment of the scanning, operation, and visual field mapping aspect of the present invention of the perimeter.
Figure 2:
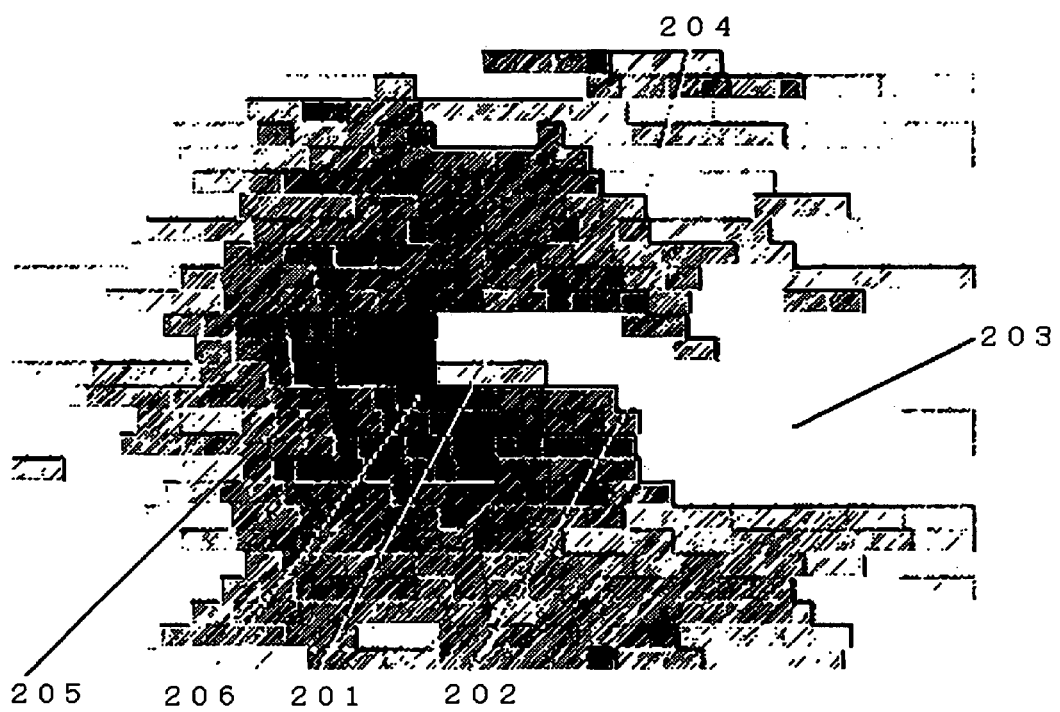
FIG. 2 is an image demonstrating an embodiment of the visual field mapping image generated by a preferred scanning of the present invention of the perimeter.

The detailed explanation of the present invention of a perimeter, an operational method of a perimeter, a program for realizing a perimeter, and a computer-readable recorded medium will be disclosed as below while referring to the drawings.

Figure 3:
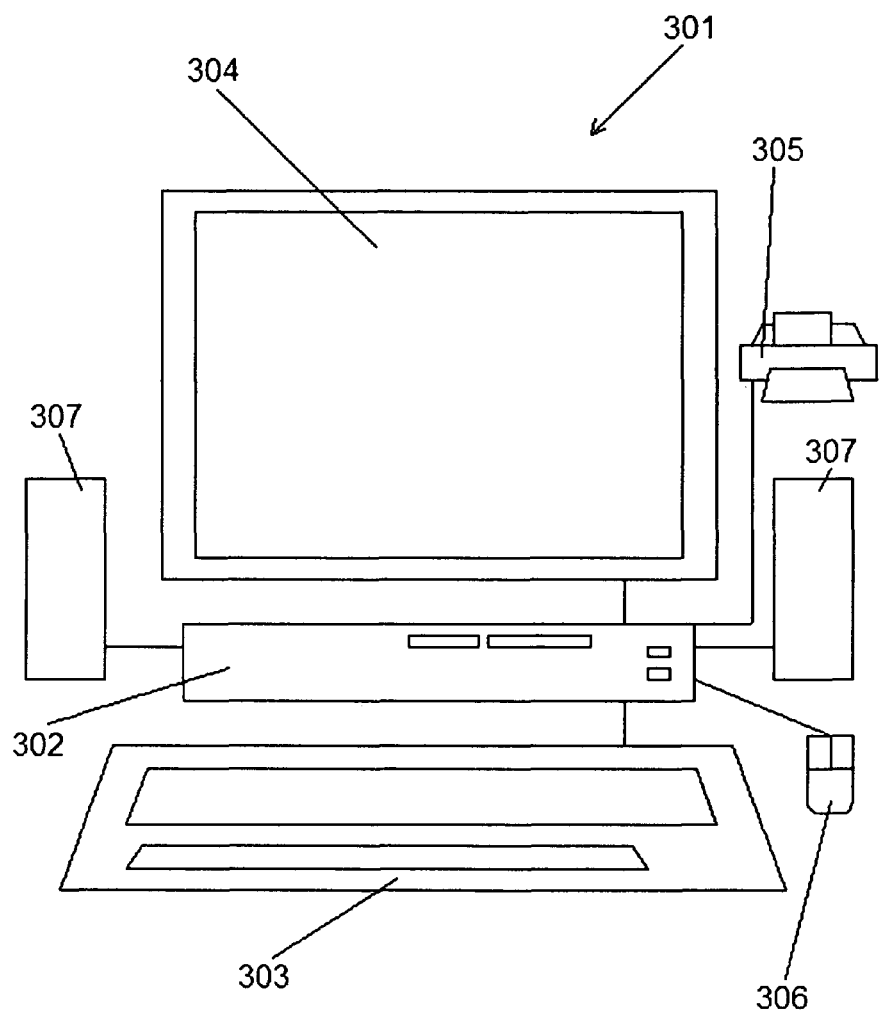
FIG. 3 is a diagram showing a preferred embodiment of the system of the present invention of the perimeter.
Figure 6:
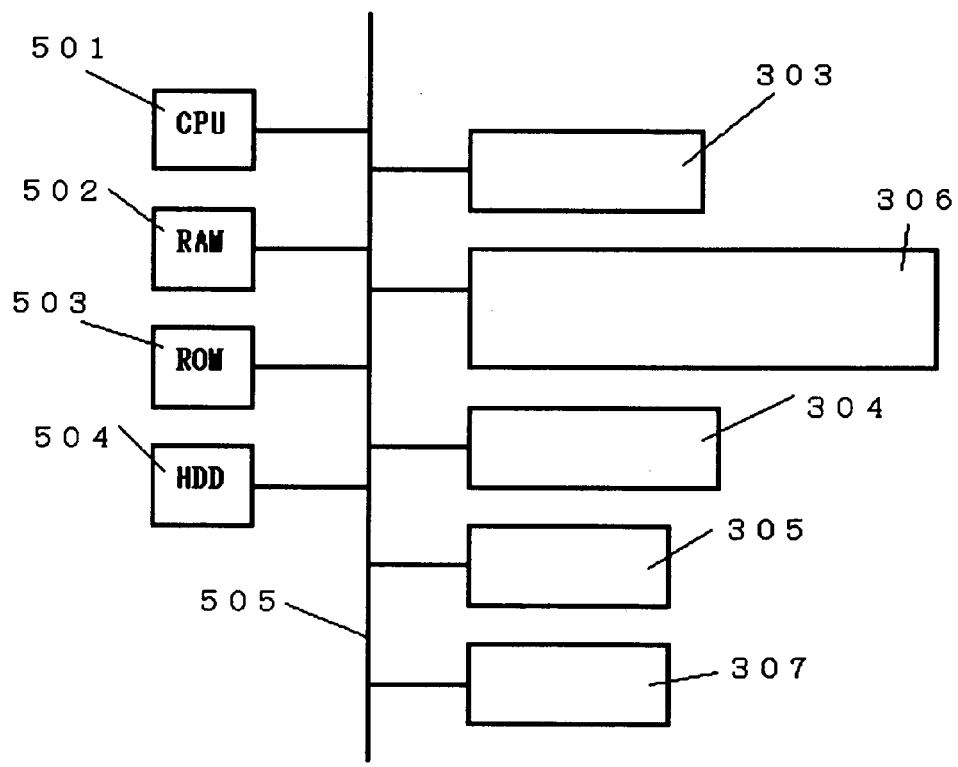
FIG. 6 is a block diagram showing a preferred embodiment of the hardware configuration of the CPU in the present invention of the perimeter.

Firstly, a setup of the present invention of the perimeter is described referring to FIG. 3 and FIG. 6.

FIG. 3 shows an embodiment of the system of the present invention of the perimeter.

FIG. 6 shows an embodiment of the hardware configuration of the CPU 501 in the present invention of the perimeter.

FIG. 3 shows a computer system 301 diagrammatically.

The present invention of the perimeter is realized by the computer system 301 carrying out a program for realizing a perimeter.

As shown in FIG. 3, the computer system 301 realizing an embodiment of the present invention of the perimeter includes a main unit 302 that is equipped with a CPU (Central Processing Unit) 501, etc., which will be mentioned later, a keyboard 303, (if necessary, a mouse 306), a display 304, and a printer 305 (and if necessary, a speaker 307 too).

Next, an embodiment of the hardware configuration of the CPU 501 in the present invention of the perimeter is described referring to FIG. 6.

The CPU 501 in the present invention of the perimeter is configured specifically including:

a microprocessor such as the CPU 501, a RAM (Random Access Memory) 502,
a ROM (Read Only Memory) 503, a HDD (Hard Disc Drive) 504, a keyboard 303,
a mouse 306, a display 304, a printer 305, a speaker 307, and a communications interface.

These parts are connected via a bus 505.

(The HDD 504 is connected through the input-output interface to the bus 505.)

The keyboard 303 is connected through the input-output interface to the bus 505, which enables output to the CPU 501 of input by the keyboard 303.

The display 304 is connected through the input-output interface to the bus 505, which enables output to the display 304 of image data input from the CPU 501.

The printer 305 is connected through the input-output interface to the bus 505, which enables output by the printer 305 of input from the CPU 501.

(The speaker 307 is connected through the input-output interface to the bus 505, which enables output by the speaker 307 of input from the CPU 501.)

(The mouse 306 is connected through the input-output interface to the bus 505, which enables output to the CPU 501 of input through the mouse 306.)

The CPU 501 carries out operations characteristic of an embodiment of the present invention, by loading onto the RAM 502 a program, which is stored in the HDD (Hard Disc Drive) 504, for realizing the present invention of a perimeter.

The CPU 501 carries out controls, and kinds of arithmetic processing, of the present invention of the perimeter, according to a program for realizing the present invention of the perimeter.

The CPU 501 controls display processing of the display 304 (an example of the output device). (Specifically, the CPU 501, for example, displaying and controlling the fixation image and visual target, and generating the visual field mapping image from the data obtained by the present invention of the perimeter.)

The CPU 501 controls the present invention of the perimeter according to input by the keyboard 303 (an example of the input device).

The CPU 501 can control the printer 305 and the like so as to output the visual field mapping image, etc. that are generated based on the data obtained from the perimeter.

(If necessary,
the CPU 501 may control the speaker 307 (an example of the output device) to produce output (for example, according to input by an input device such as the keyboard 303 or the like, or, for example, when the scan line is changed in the visual field scanning, or, for example, when the visual field mapping image is output, or the like).)

(The CPU 501 may control the present invention of the perimeter according to input from the mouse 306 (an example of the input device).)

The keyboard 303 (and if necessary, the mouse 306) and the display 304 are used as user interfaces in the present invention of the perimeter.

The keyboard 303 is used, for example, as a device for input (the input device). (If necessary, the mouse 306 is used as a device for performing various kinds of operations of input to the display screen of the display 304.)

The display 304 is a display device (the output device), for example, of a LCD (Liquid Crystal Display), a CRT (Cathode Ray Tube), or the like, which scans a visual field in accordance with the present invention of the perimeter, and displays a visual field mapping image generated by the present invention of the perimeter.

(If necessary, various screens such as an operation screen and a setting screen may be displayed on the display 304.)

(If necessary, a dome is configured to be used as a screen for the visual field scanning. In such a case, display of the visual target may be configured to be controlled in a projective manner, in substitution for the display 304.)

And when the CPU 501 is connected to communications network such as the Internet and a LAN (Local Area Network), the communications interface can be equipped with a network adapter such as a LAN card or communications equipment such as a modem, in order to establish data communication among the network. In such a case, by installing on the network a server storing a program for realizing the present invention of the perimeter, and configuring the CPU 501 as a client terminal of the server, the operation of the present invention of the perimeter can be carried out by the perimeter.

A program for realizing the present invention of the perimeter can be stored on any computer-readable recording media (storage media).

Examples of such recording media (storage media) are an optical disk, a magneto-optic disk (CD-ROM, DVD-RAM, DVD-ROM, MO, etc.), a magnetic-storage device (hard disk, Floppy Disk™, ZIP, etc.), a semiconductor memory, etc.

Next, the detailed explanation regarding the present invention of a perimeter, operational method of a perimeter, and program for realizing a perimeter will be described while referring to FIG. 1, FIG. 4 and FIG. 5, as below.

FIG. 1 shows an embodiment of the scanning, operation, and visual field mapping aspect of the present invention of the perimeter.

Figure 4:
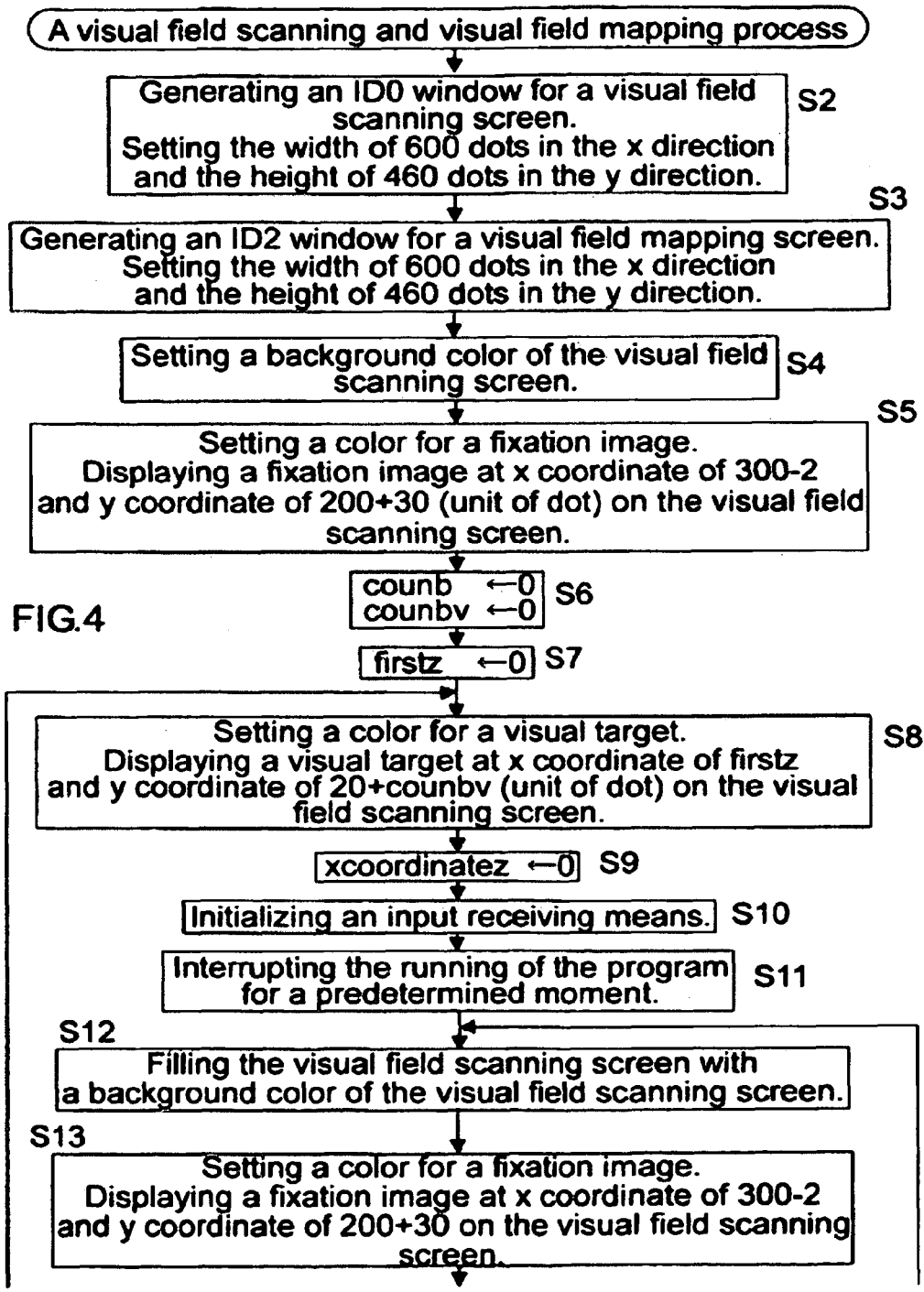
FIG. 4 is a flow chart showing a preferred embodiment of the visual field scanning and visual field mapping process of the present invention of the perimeter.
Figure 5:
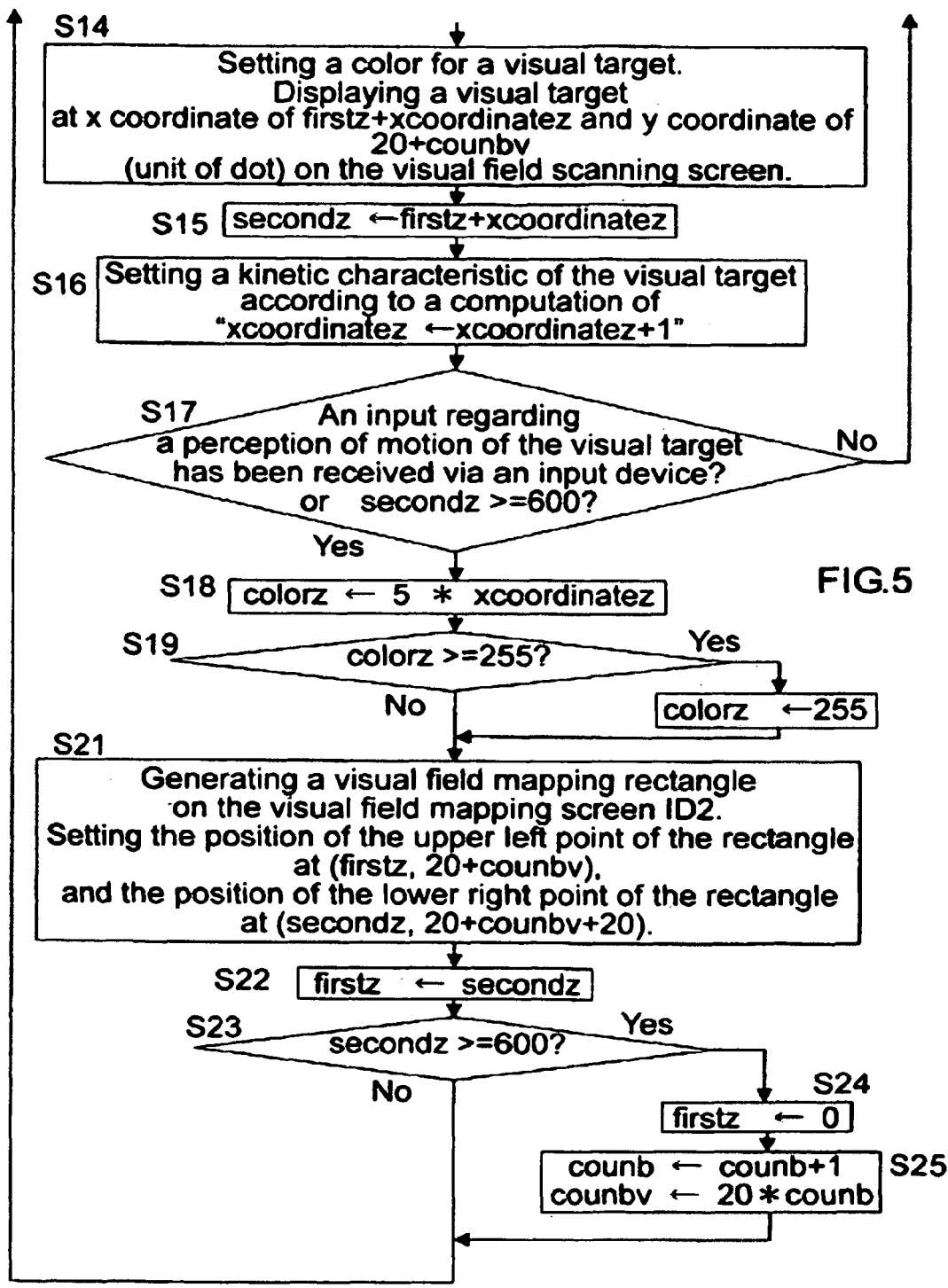
FIG. 5 is a flow chart showing a preferred embodiment of the visual field scanning and visual field mapping process of the present invention of the perimeter.

FIG. 4 and FIG. 5 show an embodiment of the visual field scanning and visual field mapping process of the present invention of the perimeter.

First, referring to FIG. 1, an embodiment of the scanning, operation, and visual field mapping aspect of the present invention of the perimeter is described in detail.

A CPU 501 generates a visual field scanning screen 1 on an output device (for example, a display 304).

The CPU 501 displays a fixation image 2 at a predetermined position on the visual field scanning screen 1 in accordance with a program for realizing the present invention of the perimeter.

The fixation image 2 is to be fixated by an eye of a subject during visual field scanning.

The CPU 501 sets, in the visual field scanning screen 1, a plurality of scan lines according to the program for realizing the present invention of the perimeter. For example, the CPU 501 arranges from an upper side of the screen a visual target scan line 3, a visual target scan line 4, . . . , and a visual target scan line 5 in order, each with a predetermined spacing (for example, in the y direction).

The CPU 501 does not display such scan lines on the visual field scanning screen 1, since each of them is set as a path of a visual target in the visual field scanning.

(Although visual target scan lines are horizontally set in FIG. 1, they may be set with other directionality.)

The CPU 501 displays first, for example, a visual target 6 statically, at a left side of the visual field scanning screen 1 on the visual target scan line 3, for a predetermined moment in accordance with the program for realizing the present invention of the perimeter.

And then, the CPU 501 carries out a display control of transforming the visual target 6 into a kinetic visual target and making it move rightward at a predetermined constant velocity.

If an input made when movement of the kinetic visual target has first been perceived by the subject's visual field (more specifically, an input made by a momentary press of, for example, the space key of a keyboard 303) is received through an input device (for example, a keyboard 303 and the like), the CPU 501 displays the kinetic visual target statically at the position at that instant of the kinetic visual target, for example, at the position of a visual target 7, for a predetermined moment (for example, for the same amount of time as the visual target 6 was statically displayed for).

At that time, the CPU 501 stores the display positions of the visual target 6 and the visual target 7, (and if necessary, for example, the distance between the visual target scan line 3 and visual target scan line 4,)(and if necessary, for example, relative locations of the fixation image 2, visual target 6, and visual target 7,) on a memory device (for example, such as a RAM 502, a HDD 504, etc.).

The CPU 501 generates a visual field mapping screen 16 on an output device (for example, the display 304). (The visual field mapping screen 16 may be generated on the output device when the CPU 501 generates the visual field scanning screen 1 on the output device.)

The CPU 501 reads out the display positions of the visual target 6 and visual target 7 (and if necessary, for example, the distance between the visual target scan line 3 and visual target scan line 4,)(and if necessary, for example, relative locations of the fixation image 2, visual target 6, and visual target 7), which are stored on the memory device (for example, such as the RAM 502, the HDD 504, etc.).

The CPU 501 forms and displays a visual field mapping rectangle 18 on the visual field mapping screen 16, based on the readout positions of the visual target 6 and visual target 7 (and if necessary, based, for example, on the distance between the visual target scan line 3 and visual target scan line 4,)(and if necessary, based, for example, on relative locations of the fixation image 2, visual target 6, and visual target 7).

The width of the visual field mapping rectangle 18 is formed based on the display positions of the visual target 6 and the visual target 7, by the CPU 501. The height of the visual field mapping rectangle 18 is formed based, for example, on the distance between the visual target scan line 3 and visual target scan line 4, by the CPU 501.

The display position of the visual field mapping rectangle 18 on the visual field mapping screen 16 is determined based on the display positions of the visual target 6 and visual target 7 (and if necessary, based, for example, on relative locations of the fixation image 2, visual target 6, and visual target 7), by the CPU 501.

The CPU 501 fills the visual field mapping rectangle 18 with, for example, a green (another kind of color may be used for the filling), in accordance with the program for realizing the present invention of the perimeter.

In the filling, the CPU 501 reads out the distance between the visual target 6 and visual target 7 which is calculated through an arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 18 with a green whose brightness is increased according to length of the distance between the visual target 6 and visual target 7. (The brightness may be set decreasing according to the length of the distance.)

As described above, the CPU 501 displays the visual target 7 statically on the visual field scanning screen 1 for a predetermined moment, and then the CPU 501 carries out a display control of transforming the visual target 7 into a kinetic visual target and making it move rightward at a predetermined constant velocity (for example, at the same velocity as the CPU 501, transforming the statically displayed visual target 6 into the kinetic visual target, made it move on the visual field scanning screen 1 at), in accordance with the program for realizing the present invention of the perimeter.

If an input made when movement of the kinetic visual target has first been perceived by the subject's visual field (more specifically, an input made by a momentary press of, for example, the space key of the keyboard 303) is received through the input device (for example, the keyboard 303 and the like), the CPU 501 displays the kinetic visual target statically at the position at that instant of the kinetic visual target, for example, at the position of a visual target 8, for a predetermined moment (for example, for the same amount of time as the visual target 6 was statically displayed for).

At that time, the CPU 501 stores the display positions of the visual target 7 and the visual target 8, and, for example, the distance between the visual target scan line 3 and visual target scan line 4, (and if necessary, for example, relative locations of the fixation image 2, visual target 7, and visual target 8,) on the memory device (for example, such as the RAM 502, the HDD 504, etc.).

The CPU 501 reads out the display positions of the visual target 7 and visual target 8 and, for example, the distance between the visual target scan line 3 and visual target scan line 4 (and if necessary, for example, relative locations of the fixation image 2, visual target 7, and visual target 8), which are stored on the memory device (for example, such as the RAM 502, the HDD 504, etc.).

The CPU 501 forms and displays a visual field mapping rectangle 19 on the visual field mapping screen 16, based on the readout positions of the visual target 7 and visual target 8, and based, for example, on the distance between the visual target scan line 3 and visual target scan line 4 (and if necessary, based, for example, on relative locations of the fixation image 2, visual target 7, and visual target 8).

The width of the visual field mapping rectangle 19 is formed based on the display positions of the visual target 7 and the visual target 8, by the CPU 501. The height of the visual field mapping rectangle 19 is formed based, for example, on the distance between the visual target scan line 3 and visual target scan line 4, by the CPU 501.

The display position of the visual field mapping rectangle 19 on the visual field mapping screen 16 is determined based on the display positions of the visual target 7 and visual target 8 (and if necessary, based, for example, on relative locations of the fixation image 2, visual target 7, and visual target 8), by the CPU 501.

The CPU 501 fills the visual field mapping rectangle 19 with, for example, a green (another kind of color may be used for the filling), in accordance with the program for realizing the present invention of the perimeter.

In the filling, the CPU 501 reads out the distance between the visual target 7 and visual target 8 which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 19 with a green whose brightness is increased according to length of the distance between the visual target 7 and visual target 8. (The brightness may be set decreasing according to the length of the distance.)

As already described, the CPU 501 displays the visual target 8 statically on the visual field scanning screen 1 for a predetermined moment, and then the CPU 501 carries out a display control of transforming the visual target 8 into a kinetic visual target and making it move rightward at a predetermined constant velocity (for example, at the same velocity as the CPU 501, transforming the statically displayed visual target 6 into the kinetic visual target, made it move on the visual field scanning screen 1 at), in accordance with the program for realizing the present invention of the perimeter.

By iterating the similar processing, the CPU 501 is now, for example, supposed to carry out a display control of transforming a visual target 9 into a kinetic visual target and making it move rightward at a predetermined constant velocity (for example, at the same velocity as the CPU 501, transforming the statically displayed visual target 6 into the kinetic visual target, made it move on the visual field scanning screen 1 at), in accordance with the program for realizing the present invention of the perimeter.

If the kinetic visual target exceeds a right edge on the visual field scanning screen 1, a position 3A, the CPU 501 detects that event through the arithmetic unit and stores a display position of the visual target 9, the position 3A, and, for example, the distance between the visual target scan line 3 and visual target scan line 4 (and if necessary, for example, relative locations of the fixation image 2, the visual target 9, and the position 3A), on the memory device (for example, such as the RAM 502, the HDD 504, etc.).

The CPU 501 reads out the display positions of the visual target 9 and position 3A, and, for example, the distance between the visual target scan line 3 and visual target scan line 4 (and if necessary, for example, relative locations of the fixation image 2, visual target 9, and position 3A), which are stored on the memory device (for example, such as the RAM 502, the HDD 504, etc.).

The CPU 501 forms and displays a visual field mapping rectangle 20 on the visual field mapping screen 16, based on the readout positions of the visual target 9 and position 3A, and based, for example, on the distance between the visual target scan line 3 and visual target scan line 4 (and if necessary, based, for example, on relative locations of the fixation image 2, visual target 9, and position 3A).

The width of the visual field mapping rectangle 20 is formed based on the display positions of the visual target 9 and the position 3A, by the CPU 501. The height of the visual field mapping rectangle 20 is formed based, for example, on the distance between the visual target scan line 3 and visual target scan line 4, by the CPU 501.

The display position of the visual field mapping rectangle 20 on the visual field mapping screen 16 is determined based on the display positions of the visual target 9 and position 3A (and if necessary, based, for example, on relative locations of the fixation image 2, visual target 9, and position 3A), by the CPU 501.

The CPU 501 fills the visual field mapping rectangle 20 with, for example, a green (another kind of color may be used for the filling), in accordance with the program for realizing the present invention of the perimeter.

In the filling, the CPU 501 reads out the distance between the visual target 9 and position 3A which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 20 with a green whose brightness is increased according to length of the distance between the visual target 9 and position 3A. (The brightness may be set decreasing according to the length of the distance.)

As already described, if the visual target, starting rightward kinetic movement from the position of the visual target 9, exceeds the right edge on the visual field scanning screen 1, the position 3A, the CPU 501 detects that event through the arithmetic unit and, in accordance with the program for realizing the present invention of the perimeter, switches the scan line to a visual target scan line 4 and (if necessary, after waiting a predetermined moment) displays a visual target 10 statically, at a left side of the visual field scanning screen 1 on the visual target scan line 4, for a predetermined moment (for example, for the same amount of time as the visual target 6 was statically displayed for).

And then the CPU 501 carries out a display control of transforming the visual target 10 into a kinetic visual target and making it move rightward at a predetermined constant velocity (for example, at the same velocity as the CPU 501, transforming the statically displayed visual target 6 into the kinetic visual target, made it move on the visual field scanning screen 1 at), in accordance with the program for realizing the present invention of the perimeter.

If an input made when movement of the kinetic visual target has first been perceived by the subject's visual field (more specifically, an input made by a momentary press of, for example, the space key of the keyboard 303) is received through the input device (for example, the keyboard 303 and the like), the CPU 501 displays the kinetic visual target statically at the position at that instant of the kinetic visual target, for example, at the position of a visual target 11, for a predetermined moment (for example, for the same amount of time as the visual target 6 was statically displayed for).

At that time, the CPU 501 stores the display positions of the visual target 10 and the visual target 11, and, for example, the distance between the visual target scan line 3 and visual target scan line 4 (that is, for example, a distance between the visual target scan line now undergoing scanning and its adjacent visual target scan line for which scanning was completed), (and if necessary, for example, relative locations of the fixation image 2, visual target 10, and visual target 11,) on the memory device (for example, such as the RAM 502, the HDD 504, etc.).

The CPU 501 reads out the display positions of the visual target 10 and visual target 11 and, for example, the distance between the visual target scan line 3 and visual target scan line 4 (that is, for example, the distance between the visual target scan line now undergoing scanning and its adjacent visual target scan line for which scanning was completed) (and if necessary, for example, relative locations of the fixation image 2, visual target 10, and visual target 11), which are stored on the memory device (for example, such as the RAM 502, the HDD 504, etc.).

The CPU 501 forms and displays a visual field mapping rectangle 21 on the visual field mapping screen 16, based on the readout positions of the visual target 10 and visual target 11, and based, for example, on the distance between the visual target scan line 3 and visual target scan line 4 (that is, for example, the distance between the visual target scan line now undergoing scanning and its adjacent visual target scan line for which scanning was completed) (and if necessary, based, for example, on relative locations of the fixation image 2, visual target 10, and visual target 11).

The width of the visual field mapping rectangle 21 is formed based on the display positions of the visual target 10 and the visual target 11, by the CPU 501. The height of the visual field mapping rectangle 21 is formed based, for example, on the distance between the visual target scan line 3 and visual target scan line 4 (that is, for example, the distance between the visual target scan line now undergoing scanning and its adjacent visual target scan line for which scanning was completed), by the CPU 501.

The display position of the visual field mapping rectangle 21 on the visual field mapping screen 16 is determined based on the display positions of the visual target 10 and visual target 11 (and if necessary, based, for example, on relative locations of the fixation image 2, visual target 10, and visual target 11), by the CPU 501.

The CPU 501 fills the visual field mapping rectangle 21 with, for example, a green (another kind of color may be used for the filling), in accordance with the program for realizing the present invention of the perimeter.

In the filling, the CPU 501 reads out the distance between the visual target 10 and visual target 11 which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 21 with a green whose brightness is increased according to length of the distance between the visual target 10 and visual target 11. (The brightness may be set decreasing according to the length of the distance.)

As already explained, the CPU 501 displays the visual target 11 statically on the visual field scanning screen 1 for a predetermined moment, and then the CPU 501 carries out a display control of transforming the visual target 11 into a kinetic visual target and making it move rightward at a predetermined constant velocity (for example, at the same velocity as the CPU 501, transforming the statically displayed visual target 6 into the kinetic visual target, made it move on the visual field scanning screen 1 at), in accordance with the program for realizing the present invention of the perimeter.

If an input made when movement of the kinetic visual target has first been perceived by the subject's visual field (more specifically, an input made by a momentary press of, for example, the space key of the keyboard 303) is received through the input device (for example, the keyboard 303 and the like), the CPU 501 displays the kinetic visual target statically at the position at that instant of the kinetic visual target, for example, at the position of a visual target 12, for a predetermined moment (for example, for the same amount of time as the visual target 6 was statically displayed for).

At that time, the CPU 501 stores the display positions of the visual target 11 and the visual target 12, and, for example, the distance between the visual target scan line 3 and visual target scan line 4 (that is, for example, the distance between the visual target scan line now undergoing scanning and its adjacent visual target scan line for which scanning was completed), (and if necessary, for example, relative locations of the fixation image 2, visual target 11, and visual target 12,) on the memory device (for example, such as the RAM 502, the HDD 504, etc.).

The CPU 501 reads out the display positions of the visual target 11 and visual target 12 and, for example, the distance between the visual target scan line 3 and visual target scan line 4 (that is, for example, the distance between the visual target scan line now undergoing scanning and its adjacent visual target scan line for which scanning was completed) (and if necessary, for example, relative locations of the fixation image 2, visual target 11, and visual target 12), which are stored on the memory device (for example, such as the RAM 502, the HDD 504, etc.).

The CPU 501 forms and displays a visual field mapping rectangle 22 on the visual field mapping screen 16, based on the readout positions of the visual target 11 and visual target 12, and based, for example, on the distance between the visual target scan line 3 and visual target scan line 4 (that is, for example, the distance between the visual target scan line now undergoing scanning and its adjacent visual target scan line for which scanning was completed) (and if necessary, based, for example, on relative locations of the fixation image 2, visual target 11, and visual target 12).

The width of the visual field mapping rectangle 22 is formed based on the display positions of the visual target 11 and the visual target 12, by the CPU 501. The height of the visual field mapping rectangle 22 is formed based, for example, on the distance between the visual target scan line 3 and visual target scan line 4 (that is, for example, the distance between the visual target scan line now undergoing scanning and its adjacent visual target scan line for which scanning was completed), by the CPU 501.

The display position of the visual field mapping rectangle 22 on the visual field mapping screen 16 is determined based on the display positions of the visual target 11 and visual target 12 (and if necessary, based, for example, on relative locations of the fixation image 2, visual target 11, and visual target 12), by the CPU 501.

The CPU 501 fills the visual field mapping rectangle 22 with, for example, a green (another kind of color may be used for the filling), in accordance with the program for realizing the present invention of the perimeter.

In the filling, the CPU 501 reads out the distance between the visual target 11 and visual target 12 which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 22 with a green whose brightness is increased according to length of the distance between the visual target 11 and visual target 12. (The brightness may be set decreasing according to the length of the distance.)

As already explained, the CPU 501 displays the visual target 12 statically on the visual field scanning screen 1 for a predetermined moment, and then the CPU 501 carries out a display control of transforming the visual target 12 into a kinetic visual target and making it move rightward at a predetermined constant velocity (for example, at the same velocity as the CPU 501, transforming the statically displayed visual target 6 into the kinetic visual target, made it move on the visual field scanning screen 1 at), in accordance with the program for realizing the present invention of the perimeter.

By iterating the similar processing, the CPU 501 is now, for example, supposed to carry out a display control of transforming the visual target 13 into a kinetic visual target and making it move rightward at a predetermined constant velocity (for example, at the same velocity as the CPU 501, transforming the statically displayed visual target 6 into the kinetic visual target, made it move on the visual field scanning screen 1 at), in accordance with the program for realizing the present invention of the perimeter.

If the kinetic visual target exceeds a right edge on the visual field scanning screen 1, a position 4A, the CPU 501 detects that event through the arithmetic unit and stores a display position of the visual target 13, the position 4A, and, for example, the distance between the visual target scan line 3 and visual target scan line 4 (that is, for example, the distance between the visual target scan line now undergoing scanning and its adjacent visual target scan line for which scanning was completed) (and if necessary, for example, relative locations of the fixation image 2, the visual target 13, and the position 4A), on the memory device (for example, such as the RAM 502, the HDD 504, etc.).

The CPU 501 reads out the display positions of the visual target 13 and position 4A, and, for example, the distance between the visual target scan line 3 and visual target scan line 4 (that is, for example, the distance between the visual target scan line now undergoing scanning and its adjacent visual target scan line for which scanning was completed) (and if necessary, for example, relative locations of the fixation image 2, visual target 13, and position 4A), which are stored on the memory device (for example, such as the RAM 502, the HDD 504, etc.).

The CPU 501 forms and displays a visual field mapping rectangle 23 on the visual field mapping screen 16, based on the readout positions of the visual target 13 and position 4A, and based, for example, on the distance between the visual target scan line 3 and visual target scan line 4 (that is, for example, the distance between the visual target scan line now undergoing scanning and its adjacent visual target scan line for which scanning was completed) (and if necessary, based, for example, on relative locations of the fixation image 2, visual target 13, and position 4A).

The width of the visual field mapping rectangle 23 is formed based on the display positions of the visual target 13 and the position 4A, by the CPU 501. The height of the visual field mapping rectangle 23 is formed based, for example, on the distance between the visual target scan line 3 and visual target scan line 4 (that is, for example, the distance between the visual target scan line now undergoing scanning and its adjacent visual target scan line for which scanning was completed), by the CPU 501.

The display position of the visual field mapping rectangle 23 on the visual field mapping screen 16 is determined based on the display positions of the visual target 13 and position 4A (and if necessary, based, for example, on relative locations of the fixation image 2, visual target 13, and position 4A), by the CPU 501.

The CPU 501 fills the visual field mapping rectangle 23 with, for example, a green (another kind of color may be used for the filling), in accordance with the program for realizing the present invention of the perimeter.

In the filling, the CPU 501 reads out the distance between the visual target 13 and position 4A which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 23 with a green whose brightness is increased according to length of the distance between the visual target 13 and position 4A. (The brightness may be set decreasing according to the length of the distance.)

By iterating the similar processing, the CPU 501 is now, for example, supposed to carry out a display control of transforming a visual target 14 into a kinetic visual target and making it move rightward at a predetermined constant velocity (for example, at the same velocity as the CPU 501, transforming the statically displayed visual target 6 into the kinetic visual target, made it move on the visual field scanning screen 1 at), in accordance with the program for realizing the present invention of the perimeter.

If the kinetic visual target exceeds a right edge on the visual field scanning screen 1, a position 14A, the CPU 501 detects that event through the arithmetic unit and stores a display position of the visual target 14, the position 14A, and, for example, the distance between the visual target scan line 3 and visual target scan line 4 (that is, for example, a distance between the visual target scan line now undergoing scanning and its adjacent visual target scan line for which scanning was completed) (and if necessary, for example, relative locations of the fixation image 2, the visual target 14, and the position 14A), on the memory device (for example, such as the RAM 502, the HDD 504, etc.).

The CPU 501 reads out the display positions of the visual target 14 and position 14A, and, for example, the distance between the visual target scan line 3 and visual target scan line 4 (that is, for example, the distance between the visual target scan line now undergoing scanning and its adjacent visual target scan line for which scanning was completed) (and if necessary, for example, relative locations of the fixation image 2, visual target 14, and position 14A), which are stored on the memory device (for example, such as the RAM 502, the HDD 504, etc.).

The CPU 501 forms and displays a visual field mapping rectangle 24 on the visual field mapping screen 16, based on the readout positions of the visual target 14 and position 14A, and based, for example, on the distance between the visual target scan line 3 and visual target scan line 4 (that is, for example, the distance between the visual target scan line now undergoing scanning and its adjacent visual target scan line for which scanning was completed) (and if necessary, based, for example, on relative locations of the fixation image 2, visual target 14, and position 14A).

The width of the visual field mapping rectangle 24 is formed based on the display positions of the visual target 14 and the position 14A, by the CPU 501. The height of the visual field mapping rectangle 24 is formed based, for example, on the distance between the visual target scan line 3 and visual target scan line 4 (that is, for example, the distance between the visual target scan line now undergoing scanning and its adjacent visual target scan line for which scanning was completed), by the CPU 501.

The display position of the visual field mapping rectangle 24 on the visual field mapping screen 16 is determined based on the display positions of the visual target 14 and position 14A (and if necessary, based, for example, on relative locations of the fixation image 2, visual target 14, and position 14A), by the CPU 501.

The CPU 501 fills the visual field mapping rectangle 24 with, for example, a green (another kind of color may be used for the filling), in accordance with the program for realizing the present invention of the perimeter.

In the filling, the CPU 501 reads out the distance between the visual target 14 and position 14A which is calculated through the arithmetic unit and stored on the memory device (for example, such as the RAM 502, the HDD 504, etc.), and, carrying out an arithmetic operation by the arithmetic unit, converts the value of the distance into a value for specifying (according to the value of the distance) the color code of, for example, G in the RGB.

The CPU 501 fills the visual field mapping rectangle 24 with a green whose brightness is increased according to length of the distance between the visual target 14 and position 14A. (The brightness may be set decreasing according to the length of the distance.)

(In order to clarify the positions of the scotoma 201 and blind spot 203 shown in the visual field mapping screen 16 in relation to the display position of the fixation image 2 on the visual field scanning screen 1,)

The position on the visual field mapping screen 16, which corresponds to the display position of the fixation image 2 on the visual field scanning screen 1, may be explicitly shown by a fixation image on the visual field mapping screen 17 in the visual field mapping screen 16.

A cluster of visual field mapping rectangles 15, which is to be generated as a result of a visual field scanning, is shown as a reference to the precise positional representation in the visual field scanning screen 1.

A cluster of visual field mapping rectangles 25, which is to be generated as a result of a visual field scanning, is shown as a reference to the precise positional representation in the visual field mapping screen 16.

Regarding a visual field scanning and visual field mapping process carried out by the CPU 501 in accordance with a program for realizing the present invention of the perimeter, the detailed explanation will be disclosed as below while referring to FIG. 4 and FIG. 5.

FIG. 4 and FIG. 5 are flow charts showing a visual field scanning and visual field mapping process to be carried out by a computer shown in FIG. 6.

At the step of S2 of the visual field scanning and visual field mapping process, a CPU 501 generates an ID0 window for a visual field scanning screen 1, on an output device (for example, a display 304).

The CPU 501 sets its width of 600 dots in the x direction and its height of 460 dots in the y direction.

Hereinafter, the positions are described, in explanation of the visual field scanning screen 1, assuming that the position of the upper left corner of the visual field scanning screen 1 shall be at x coordinate of 0 dot and y coordinate of 0 dot and that an x coordinate axis shall be generated rightward from the upper left corner of the visual field scanning screen 1 and a y coordinate axis shall be generated downward from the upper left corner of the visual field scanning screen 1.

At the step of S3, the CPU 501 generates an ID2 window for a visual field mapping screen 16, on an output device (for example, a display 304).

The CPU 501 sets its width of 600 dots in the x direction and its height of 460 dots in the y direction.

Hereinafter, in the explanation of the visual field mapping screen 16, positions are described assuming that the position of the upper left corner of the visual field mapping screen 16 shall be at x coordinate of 0 dot and y coordinate of 0 dot and that an x coordinate axis shall be generated rightward from the upper left corner of the visual field mapping screen 16 and a y coordinate axis shall be generated downward from the upper left corner of the visual field mapping screen 16.

At the step of S4, the CPU 501 sets a background color of the visual field scanning screen 1.

At the step of S5, the CPU 501 sets a color, size, and shape for a fixation image, and displays a fixation image 2, for example, at x coordinate of 300−2 and y coordinate of 200+30 (unit of dot) on the visual field scanning screen 1.

At the step of S6, the CPU 501 initializes the values of a variable counb and a variable counbv to be 0. (For example, a variable counbv is associated with the position in the y direction of a visual target scan line, and 20+counbv designate the y coordinate of a visual target scan line as, for example, at S8 and S14.)

(By initializing the value of the variable counbv at 0, the position of a visual target scan line is set at an initial position.)

At the step of S7, the CPU 501 initializes the value of a variable firstz at 0. (A value of the variable firstz is a display position of a visual target that is stored, through the static display position storing means, on the memory device, equaling to the x coordinate of a left side of a visual field mapping rectangle (for example, each of visual field mapping rectangles 18, 19, 20, 21, 22, 23, and 24) generated at S21.)

At the step of S8, the CPU 501 sets a color, size, and shape for a visual target. The CPU 501 displays a visual target, for example, at x coordinate of firstz dots and y coordinate of 20+counbv dots on the visual field scanning screen 1.

(Forming a part of a visual target scan line setting means.)
(The variable firstz forms a part of the static display position storing means.)

At the step of S9, the CPU 501 initializes the value of a variable xcoordinatez at 0 (the variable xcoordinatez is a variable for displaying and controlling a visual target kinetically as at S16).

(Forming a part of a scanning continuation means of the same scan line.)

(Forming a part of a scanning switching means to the next scan line.)

At the step of S10, the CPU 501 initializes an input receiving means.

At the step of S11, the CPU 501, for example, interrupts the running of the program for a predetermined moment to display the visual target statically.

(Forming a part of a statically displaying and controlling means.)

(Forming a part of a scanning continuation means of the same scan line.)

(Possibly forming a part of a scanning switching means to the next scan line.)

At the step of S12, the CPU 501 fills the visual field scanning screen 1 with the background color (of the visual field scanning screen 1) set at S4.

At the step of S13, the CPU 501 sets a color, size, and shape for a fixation image.

The CPU 501 displays a fixation image 2, for example, at x coordinate of 300−2 dots and y coordinate of 200+30 dots on the visual field scanning screen 1.

At the step of S14, the CPU 501 sets a color, size, and shape for a visual target.

The CPU 501 displays a visual target, for example, at x coordinate of firstz+xcoordinatez dots and y coordinate of 20+counbv dots on the visual field scanning screen 1.

(Forming a part of a visual target scan line setting means.)

(Forming a part of a kinetic display and control starting means.)

At the step of S15, the CPU 501 carries out a computation of firstz+xcoordinatez through an arithmetic unit, the result of which is substituted into a variable secondz and stored on a memory device (for example, such as a RAM 502, a HDD 504, etc.).

(The variable secondz forms a part of a detection position storing means if at S22 and secondz>=600 does not hold.)

(If a visual target exceeds a right edge of the visual field scanning screen 1 and secondz>=600 is satisfied, the detection position storing means may store, in a variable secondz, the x coordinate of the right edge of the visual field scanning screen 1 in substitution for a position of a visual target at the time of the detection by a detecting means, as at S17 and S21.)

(At S21, the variable secondz forms a part of a visual field mapping rectangle forming means, equaling to the x coordinate of a right side of a visual field mapping rectangle (for example, each of visual field mapping rectangles 18, 19, 20, 21, 22, 23, and 24) generated at S21.)

(At S23, the variable secondz forms a part of a scanning switching means to the next scan line.)

At the step of S16, the CPU 501 increments the value of xcoordinatez by, for example, one and stores the result on a memory device (for example, such as a RAM 502, a HDD 504, etc.).

Such an increment is set so as to cause a visual target to take on a kinetic characteristic (the value of the increment may be set by another value).

(Forming a part of a kinetic display and control starting means.)

(The variable xcoordinatez is a distance storing means. (but if a visual target exceeds a right edge of the visual field scanning screen 1 and secondz>=600 is satisfied, a distance from the position of the right edge of the visual field scanning screen 1 to the position of a visual target, which had been statically displayed for a predetermined moment a little before its reaching the right edge, may be set to be stored in a variable xcoordinatez, as at S17 and S18.))

(And a value stored in a variable xcoordinatez is the value representing the length in width of a visual field mapping rectangle generated at S21, and converted into a numeric value for designating a color with which the visual field mapping rectangle is filled.)

(If necessary, a color other than above mentioned may be designated for visual field mapping rectangles adjacently generated to both ends of a scan line.)

At the step of S17, a judgment on if "an input regarding a perception of motion of the visual target has been received via an input device" or "secondz>=600 is satisfied", is made by the CPU 501.

If neither holds, the CPU 501 goes back to S12 and continues carrying out the process to give rise to a kinetic characteristic of a visual target.

(Forming a part of a kinetic display and control starting means.)

In the judgement at the step of S17 on if "an input regarding a perception of motion of the visual target has been received via an input device" or "secondz>=600 is satisfied", when the CPU 501 judges that either or both hold, the CPU 501 moves on to S18.

(Forming a part of a detecting means.)

(Forming a part of a scanning switching means to the next scan line.)

At the step of S18, the CPU 501 carries out a computation of 5* xcoordinatez through an arithmetic unit, substituting the result into a variable colorz, which is stored on a memory device (for example, such as a RAM 502, a HDD 504, etc.).

(Forming a part of a visual field mapping rectangle image processing means.)

At the step of S19, the value of a variable colorz stored on the memory device (for example, such as the RAM 502, the HDD 504, etc.) is read out by the CPU 501, and a judgement whether colorz>=255, is made through an arithmetic unit by the CPU 501.

At the step of S19, the CPU 501 moves to S21 and continues the processing if the CPU 501 judges that colorz>=255 does not hold.

(Forming a part of a visual field mapping rectangle image processing means.)

When at the step of S19 the CPU 501 judges that colorz>=255 holds, the CPU 501 updates the value of colorz with 255, stores that value in a memory device (for example, such as a RAM 502, a HDD 504, etc.), and moves on to S21, continuing the processing.

At the step of S21, the CPU 501 generates a visual field mapping rectangle (for example, any one of visual field mapping rectangles 18, 19, 20, 21, 22, 23, and 24) on the visual field mapping screen ID2.

The CPU 501 sets the position of the upper left point of the rectangle (for example, the one of visual field mapping rectangles 18, 19, 20, 21, 22, 23, and 24) at (firstz, 20+counbv), and sets the position of the lower right point of the rectangle at (secondz, 20+counbv+20).

(Forming a part of a visual field mapping rectangle forming means.)

(The "+20" in the 20+counbv+20 of the y coordinate at the lower right corner set a height of a visual field mapping rectangle, and the "20" is, for example, set in reference to the amount of an increment made to counbv at S25, that is, an interval between adjacent visual target scan lines.)

The CPU 501 fills the visual field mapping rectangle with a color whose brightness of R,G,B is, for example, 0,colorz,6, respectively.

(Forming a part of a visual field mapping rectangle image processing means.)

At the step of S22, the CPU 501 updates the content of a variable firstz with the content stored in a variable secondz, and stores that value on a memory device (for example, such as a RAM 502, a HDD 504, etc.).

(The variable secondz forms a part of a detection position storing means if "at S22" and "secondz>=600 does not hold.")

(The rewrote content of a variable firstz forms a part of a statically displaying and controlling means if "at S22" and "secondz>=600 does not hold.")

(Forming a part of a scanning continuation means of the same scan line if "at S22" and "secondz>=600 does not hold.")

At the step of S23, the CPU 501 judges, via an arithmetic unit, whether secondz>=600.

If the CPU 501 judges, at S23, that secondz>=600 does not hold, the CPU 501 goes back to S8, continuing the processing.

(Forming a part of a scanning continuation means of the same scan line.)

If the CPU 501 judges, at S23, that secondz>=600 is satisfied, the CPU 501 initializes, at S24, the value of a variable firstz at zero (forming a part of a scanning switching means to the next scan line), and increments, at S25, the value of a variable counb by, for example, 1, which is stored on a memory device (for example, such as a RAM 502, a HDD 504, etc.), and the CPU 501 reads out the value of the counb stored on the memory device (for example, such as the RAM 502, the HDD 504, etc.), carries out a computation of 20*counb, substitutes the result into a variable counbv (forming a part of a visual target scan line setting means,) (forming a part of a scanning switching means to the next scan line), which is stored on a memory device (for example, such as a RAM 502, a HDD 504, etc.), and then the CPU 501 goes back to S8, continuing the processing.

What is claimed is:

1. An apparatus for examining a visual field comprising:
    means for generating, on an output device, a visual field scanning screen for scanning a visual field of a subject;
    means for displaying and controlling a fixation image to be fixated by said subject, during a visual field scanning, on the visual field scanning screen generated by said visual field scanning screen generating means;
    means for setting a visual target scan line to scan a visual target, parallel on said visual field scanning screen;
    means for statically displaying and controlling said visual target on the visual target scan line set by said visual target scan line parallel setting means;
    means for storing, on a memory device, a position of said visual target statically displayed and controlled by said statically displaying and controlling means;
    means for stopping said static display and control of said visual target if said visual target has statically displayed and controlled for a predetermined moment by said statically displaying and controlling means;
    means for starting a kinetic scan of said visual target, along said visual target scan line, from the position stored, by said static display position storing means, in the memory device, if said static display and control of said visual target is stopped by said static display and control stopping means;
    means for, via an input device, detecting a time when said kinetic scan, started by said kinetic display and control starting means, of said visual target has first been perceived by the subject's visual field;
    means for storing, on the memory device, a position of said visual target at the time of the detection by said detecting means;
    means for storing, on the memory device, a distance from the position of said visual target displayed and controlled by said statically displaying and controlling means, to the position of said visual target at the time of the detection by said detecting means, as a piece of information which reflects a function of the visual field extending from the position of said visual target displayed and controlled by said statically displaying and controlling means, to the position of said visual target at the time of the detection by said detecting means;
    means for stopping said kinetic scan of said visual target if the time when said kinetic scan has first been perceived by the subject's visual field is detected via the input device by said detecting means;
    and scanning continuation means for, through said statically displaying and controlling means, displaying and controlling said visual target statically on said visual target scan line at the position of said visual target stored by said detection position storing means,
    and proceeding from said static display position storing means onward as above,
    and continuing the similar scan of said visual target scan line by iterating above procedure along said visual target scan line,
    in order to continue the next scan of said visual target scan line if the time when said kinetic scan has first been perceived by the subject's visual field is detected via the input device by said detecting means.

2. A program for causing a computer to realize a function comprising:
    means for generating, on an output device, a visual field scanning screen for scanning a visual field of a subject;
    means for displaying and controlling a fixation image to be fixated by said subject, during a visual field scanning, on the visual field scanning screen generated by said visual field scanning screen generating means;
    means for setting a visual target scan line to scan a visual target, parallel on said visual field scanning screen;
    means for statically displaying and controlling said visual target on the visual target scan line set by said visual target scan line parallel setting means;
    means for storing, on a memory device, a position of said visual target statically displayed and controlled by said statically displaying and controlling means;
    means for stopping said static display and control of said visual target if said visual target has statically displayed and controlled for a predetermined moment by said statically displaying and controlling means;
    means for starting a kinetic scan of said visual target, along said visual target scan line, from the position stored, by said static display position storing means, in the memory device, if said static display and control of said visual target is stopped by said static display and control stopping means;
    means for, via an input device, detecting a time when said kinetic scan, started by said kinetic display and control starting means, of said visual target has first been perceived by the subject's visual field;
    means for storing, on the memory device, a position of said visual target at the time of the detection by said detecting means;
    means for storing, on the memory device, a distance from the position of said visual target displayed and controlled by said statically displaying and controlling means, to the position of said visual target at the time of the detection by said detecting means, as a piece of information which reflects a function of the visual field extending from the position of said visual target displayed and controlled by said statically displaying and controlling means, to the position of said visual target at the time of the detection by said detecting means;
    means for stopping said kinetic scan of said visual target if the time when said kinetic scan has first been perceived by the subject's visual field is detected via the input device by said detecting means;
    and scanning continuation means for, through said statically displaying and controlling means, displaying and controlling said visual target statically on said visual target scan line at the position of said visual target stored by said detection position storing means,
    and proceeding from said static display position storing means onward as above,
    and continuing the similar scan of said visual target scan line by iterating above procedure along said visual target scan line,
    in order to continue the next scan of said visual target scan line if the time when said kinetic scan has first been perceived by the subject's visual field is detected via the input device by said detecting means.

* * * * *